United States Patent
van der Zel et al.

(10) Patent No.: US 7,988,448 B2
(45) Date of Patent: Aug. 2, 2011

(54) AESTHETIC CERAMIC VENEERED RESTORATION

(75) Inventors: Joseph Maria van der Zel, Hoorn (NL);
Petrus Gerardus Appelman, Opmeer (NL); Eric Marinus Hermanus Cornelissen, Huizen (NL); Marcel Andre de Kler, Alkmaar (NL); Jurgen Gebhardt, Lauf a.d. Pegnitz (NL)

(73) Assignee: Dentsply International, Inc., York, PA (US)

( * ) Notice: Subject to any disclaimer, the term of this patent is extended or adjusted under 35 U.S.C. 154(b) by 80 days.

(21) Appl. No.: 12/384,290

(22) Filed: Apr. 2, 2009

(65) Prior Publication Data

US 2010/0015574 A1    Jan. 21, 2010

(51) Int. Cl.
*A61K 6/02* (2006.01)
*A61C 13/09* (2006.01)

(52) U.S. Cl. ............... 433/203.1; 433/222.1; 433/202.1

(58) Field of Classification Search ............... 433/202.1, 433/203.1, 208, 212.1, 218, 222.1, 223
See application file for complete search history.

(56) References Cited

U.S. PATENT DOCUMENTS

| | | | | |
|---|---|---|---|---|
| 4,433,959 A * | 2/1984 | Faunce | ........................ | 433/222.1 |
| 4,741,699 A * | 5/1988 | Kosmos | ...................... | 433/203.1 |
| 5,308,243 A * | 5/1994 | Emmons | ..................... | 433/203.1 |
| 5,453,290 A * | 9/1995 | van der Zel | .................. | 427/2.27 |
| 5,713,994 A * | 2/1998 | Kramer et al. | ................... | 106/35 |
| 6,232,367 B1* | 5/2001 | Kobashigawa et al. | ........ | 523/116 |
| 2002/0010063 A1* | 1/2002 | Schweiger et al. | ............... | 501/5 |
| 2004/0137409 A1* | 7/2004 | Savic et al. | ................ | 433/203.1 |
| 2004/0206273 A1* | 10/2004 | Hermansson et al. | .......... | 106/35 |
| 2004/0232576 A1* | 11/2004 | Brodkin et al. | .................. | 264/16 |
| 2005/0155518 A1* | 7/2005 | Krumbholz | ..................... | 106/35 |

FOREIGN PATENT DOCUMENTS

| | | |
|---|---|---|
| DE | 197 14 178 | 10/1998 |
| EP | 1 400 232 | 3/2004 |
| WO | WO 97/45377 | 12/1997 |
| WO | WO 01/26611 | 4/2001 |

\* cited by examiner

*Primary Examiner* — Ralph A Lewis
(74) *Attorney, Agent, or Firm* — Douglas J. Hura; David A. Zdurne; Leana Levin

(57) ABSTRACT

The present invention relates to an aesthetic dental restoration having a layered structure, which dental restoration has the appearance of a natural tooth. In addition, the present invention relates to a method for preparing such dental restorations. Particularly, the invention is based on the control of interaction between opalescence and fluorescence.

17 Claims, 1 Drawing Sheet

AESTHETIC CERAMIC VENEERED RESTORATION

Figure 1:
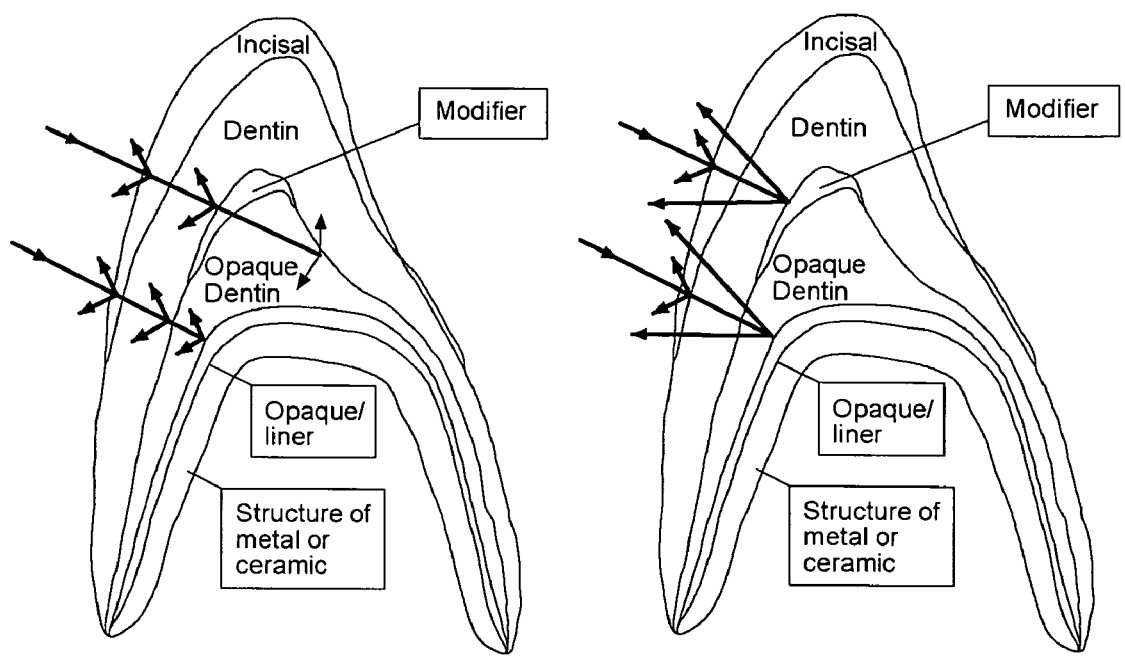

The present invention relates to aesthetic ceramic veneered dental restorations and to a process and system for producing such restoration. More particularly, the present invention is based on a process for the production of an aesthetic porcelain veneered restoration on the basis of a new shade build-up, based on a functional separation between two optical phenomena, opalescence and fluorescence.

Dental restorations have been prepared in the prior art which comprise a substructure of a metal or ceramic material, upon which substructure layers of porcelain are applied. Generally, the substructure is covered by a layer of opaque material to effect that the substructure has not an adverse effect on the appearance of the restoration in the mouth. It is described in, for instance, U.S. Pat. No. 5,453,290 that a metal substructure is covered with an opaque layer, and a dentin layer. Generally, nowadays, ceramic or metal alloy substructures are first covered by an opaque layer, followed by an opacious dentin layer, a dentin layer and finally an incisal porcelain layer.

Especially the last decades, there is a tendency to prepare dental restorations which have an appearance that differs as little as possible from the natural teeth of a person needing a dental restoration. It is also one of the primary aims of the present invention to prepare a dental restoration that will blend in naturally with the remaining dentition in the mouth of the individual needing said restoration. That is, a primary aim underlying the present invention is to provide dental restorations which have the appearance of a natural tooth.

With this aim in mind, in the prior art the dental technician has incorporated in the various layers of a dental restoration, coloring agents with the aim to adapt the color of the restoration to the color of the teeth in the mouth of the individual for which the restoration is produced. Moreover, the surfaces of the restorations were treated such that these gave the impression of natural teeth.

However, such traditional veneering ceramics have a blocky appearance, while the actual shade of the restoration comes from the material itself.

More in particular, the skilled person appreciates that the appearance of an artificial tooth is not only dependant on color and surface properties, but that also the transmission behavior of light is important. It is known that homogeneous transparent masses of porcelain with a smooth surface give a reflecting and clear appearance, while the addition of reflecting particles to the porcelain mass or a rough surface create a diffuse light scattering; the light transmission is hindered. Opalescence and fluorescence are also important features.

Dental technicians generally add sufficient amounts of fluorescent material, and particularly yttriumoxide in the porcelain material, so that a "black hole" appearance under certain lighting conditions is prevented. The fluorescent material, however, also has a slightly opaquefying effect; it creates a somewhat cloudy effect which hinders the transmission of light and which has a negative influence on the translucency of the restoration made. That is, light only partly penetrates the veneering material and is diffusely distributed inside the material, giving the restoration its "colored tooth" appearance.

Opalescense is an optic phenomenon, caused by the so-called Tyndall-effect of light absorption by particle light scattering. To introduce the impression of opalescense, it has been proposed to add blue pigments. However, such blue pigments give under different light conditions different effects.

Although the dental technician was confronted many times with the goal to produce a dental restoration that will blend naturally with the remaining dentition, so far this goal has not been totally reached. Exactly copying the shade of the adjacent teeth is a painstaking trial-and-error task and does not always lead to success because of the individuality of teeth.

The present invention aims to solve, or at least to reduce the problems encountered in the prior art. It is based on the control of opalescence and fluorescence properties in the porcelain or ceramic material used in the preparation of dental restorations.

Particularly, in a first aspect, the present invention relates to a dental restoration comprising one or more opaque layers covered by one or more other porcelain layers, the opaque layers being situated closer to the core than the other porcelain layers, wherein at least one of the opaque layers contains a fluorescent material, and wherein the one or more other porcelain layers are predominantly transparent and opalescent. That is, the fluorescence required to provide a natural appearance originates from the deeper laying layers, while the required opalescence originates from the layers closer to the surface of the dental restoration.

In a second aspect, the present invention relates to a method of layering porcelain on a structure of metal or ceramic comprising the steps of applying a first layer or first layers of an opaque liner material containing a fluorescent material and in a subsequent step applying one or more layers of a translucent, opalescent material.

U.S. Pat. No. 4,741,699 describes dental porcelain before opalescence was introduced. In this document it is aimed to match not only the color but also the fluorescence of teeth in restorations to that of natural teeth. Thereto, it requires that the inorganic pigment that causes the fluorescent effect is lower in the outer, more translucent layers, because of light absorbance by the stained porcelain. It is well known that to obtain the same fluorescent effect in porcelain it is necessary to increase the fluorescence, when other pigments are increased because of light absorption effects. The present invention, on the contrary, aims for a maximum opalescent effect, instead of uniform UV fluorescence. However, a minimum, but sufficient, amount of fluorescent effect is still obtained in the restoration of the present invention.

In accordance with the present invention, it was surprisingly found that the transparent outer layer is responsible for a deeper penetration of light to the fluorescent opaque layer where the light reflects back through the more translucent outer layer. This interaction gives a lively, natural effect, which makes the acceptance or appearance of the restoration less dependent on the obtaining of an exact copy of the shade of the adjacent teeth, as is the case with traditional veneering materials.

The fluorescent material creates a glow from deep within; the more light enters the artificial tooth, the stronger the reflection and clarity of said tooth. The opaque layer required by the present invention hence breaks light, reflects it and gives fluorescence. The fluorescent materials used are excited by UV light and send out VIS light. The light reflected and sent out by the lower opaque layer or layers amplifies the opalescence in the transparent upper layers.

By the present invention and particularly by the interaction between opalescence and fluorescence, it becomes possible to control the color and light effects in the mouth.

The present invention will be further explained with reference to the drawings in FIG. 1, wherein the principle of the invention is illustrated for a preferred embodiment.

Particularly, FIG. 1 shows at the left-hand side a standard layered restoration known from the prior art (traditional method), and at the right-hand side a preferred embodiment of the invention. In the traditional method most of the light that falls on the restoration is diffusely dispersed into the ceramic. In the method according to the present invention, the light is transferred much deeper into the more transparent opalescent layers, and especially the more transparent and opalescent incisal, dentin and opaque/dentin layers and is for a great part reflected against the strongly fluorescent opaque layer and on the strongly fluorescent modifier, which is present between the dentin and opaque/dentin layer, in such a way that it exits the ceramic, to give a very "lively" and natural appearance.

That is, the present invention involves a specific layering of porcelain on a structure of metal or ceramic to obtain a more naturally looking opalescent and fluorescent effect by functionally separating opalescence and fluorescence in that the opaque layer and, if present, a modifier layer have relatively strong fluorescence and the outer transparent layers give a strong opalescence, and have little fluorescence. It appears that when the veneering material was built-up in such a way a much more acceptable blending-in process with the rest of the dentition is experienced. The reflected light from a strongly fluorescent modifier, when present, and opaque layer interacts with the shade of the dentin layer, giving this effect.

In order to provide a sufficiently strong fluorescence, the opaque layer that contains the fluorescent material should contain said fluorescent material in a considerable amount. Preferably, the fluorescent material is present in an amount of at least 2 wt %, preferably in an amount between 2 and 5 wt %, drawn to the weight of the porcelain material wherein it is incorporated, such as in the opaque liner material.

Because opalescence is an optic phenomenon, caused by the Tyndall-effect of light absorption by particle light scattering, it is only effective in optically transparent materials. Therefore the opaquefying effect by addition of a fluorescent must possibly be avoided. Hence, the layers of translucent, opalescent material should in principle not contain fluorescent material. However, the effects of the invention are still obtained if the amount of fluorescent material in the transparent, opalescent layers is lower than 0.1 wt %, drawing to the weight of the layers forming said translucent material. Preferably, these layers contain less than 0.05 wt % fluorescent material.

The fluorescent material used can in principle be any material that is compatible with the opaque porcelain material and that is able to send out visible light. In a preferred embodiment, the fluorescent material comprises and preferably consists of yttrium oxide.

The translucent, opalescent material should preferably have a translucency of more than 30%. In a preferred embodiment the translucent, opalescent material is made of porcelain containing at least 10% of an opal glass frit. Particularly good results are obtained with transparent porcelain layers which consist of 10-100 wt % opal glass frit with the following composition in wt % drawn to the weight of the total composition: 45-70% $SiO_2$, 0-20% $Al_2O_3$, 0-20% $K_2O$, 0-15% $Na_2O$, 0-5% CaO, 0-3% MgO, 0-4% $CeO_2$, 0-4% $Tb_2O_3$, 1-10% $P_2O_5$, 0-1% $CaF_2$, 0-2% $Li_2O$, and 0-5% $Sb_2O_3$. Alternatively, equally good results are obtained with transparent porcelain layers which consist of 10-100 wt.-% opal glass frit with the following composition in wt %: 45-70% $SiO_2$, 0-20% $Al_2O_3$, 0-20% $K_2O$, 0-15% $Na_2O$, 0-5% CaO, 0-3% MgO, 0-4% $CeO_2$, 0-4% $Tb_2O_3$, 0-2% $P_2O_5$, 5-15% $CaF_2$, 0-2% $Li_2O$, and 0-5% $Sb_2O_3$.

The dental restoration of the present invention comprises at least one opaque layer that contains fluorescent material, and more to the surface of the dental restoration other porcelain layers which are transparent and opalescent. These other porcelain layers comprise at least one incisal layer, at least one dentin layer, and optionally at least one opaque/dentin layer. See in this respect FIG. 1.

In a particularly preferred embodiment, the dental restoration of the invention has a modifier containing fluorescent material present in an area between the incisal layer or layers and the dentin layer or layers and/or between the dentin layer(s) and the opaque/dentin layer(s). This modifier makes it possible to provide an even better adapted natural looking tooth.

Suitably, the modifier layer contains at least 0.1 wt % yttriumoxide as fluorescent applied between the dentin and the incisal layer.

In accordance with this aspect of the present invention, when a transparent outer layer is used and when an internal highly fluorescent material is used in-between the incisal and dentin layer, the process of blending-in with the remaining dentition takes place easily, even if the shade is not exactly copied. The shade of the modifier layer interacts with the basic dentin material to give a play of light and shades, which can also be seen when teeth are observed under different light conditions (morning, noon or evening; spring, summer, autumn or winter).

In the porcelains used to be applied to a substructure of either ceramic or a metal or a metal or metal alloy, coloring agents can be incorporated under the precondition that these do not interfere with the interaction between opalescence and fluorescence.

In the method of the present invention, the preferred opal glass frit containing composition for the translucent layers to be applied, preferably having a firing temperature that is not lower than 25° C. than the firing temperature of the basic veneering material on which it is applied. This should secure that the two materials do not react with each other.

Finally, the present invention foresees in an easy-to-use ceramic system build-up for use in the method of the present invention. This easy-to-use system ensures that the dental technician achieves the benefits and advantages mentioned for the invention without exactly needing to know all the specific effects of each separate layer. This system is embodied in TABLE A and is based on the color indications used by the dental technicians (A1-D4). In this TABLE A, the action i dentin refers to the color of the modifier layer used in the preferred embodiment of the invention, and the x-tra-incisals refer to the high opalescent layers according to the invention.

The present invention will now be further illustrated by means of the following non-limiting examples. In these examples describing the method and products of the present invention the following basis ceramic compositions were used. The first ceramic composition used is veneering porcelain C as described in U.S. Pat. No. 5,453,290. This product is sold under the trade name "Carrara" (registered trade name of Elephant Dental B. V., Hoorn, The Netherlands). The second ceramic material used is veneering porcelain A used for standard ceramic alloys and is sold under the name "Antagon" (registered trade name of Elephant Dental B. V., Hoorn, The Netherlands). Another basis veneering material S is sold under the name "Sintagon" (registered trade name of Elephant Dental B. V., Hoorn, The Netherlands) and is used for the veneering of Y-PTZ zirconia structures. In Table 1, the composition of the three basic veneering materials is given.

TABLE 1

Composition in wt. - % of three basic veneering materials

| Component | Material C | Material A | Material S |
|---|---|---|---|
| $SiO_2$ | 65.1 | 64.1 | 67.0 |
| $Al_2O_3$ | 12.5 | 14.2 | 11.0 |
| $K_2O$ | 11.6 | 11.1 | 10.1 |
| $Na_2O$ | 7.2 | 6.6 | 8.6 |
| CaO | 0.7 | 1.1 | 0.8 |
| BaO | 0.9 | 0.4 | 1.3 |
| $Sb_2O_3$ | 1.5 | 1.4 | 2.1 |
| $Li_2O$ | 0.3 | 0.2 | 0.2 |
| $F_2$ | 0.6 | 0.6 | 0.0 |
| Translucency (%) 520 nm 1x | 68.0 | 73.0 | 80.0 |
| Translucency (%) 520 nm 5x | 65.0 | 70.0 | 80.0 |
| Firing Temperature, °C. | 860 | 900 | 830 |
| Glass Transition Temperature, °C. | 460 | 460 | 480 |
| TEC μm/m · K (25 to 400° C.) | 13.7 | 12.4 | 9.4 |
| TEC μm/m · K (25 to 500° C.) | 14.7 | 12.7 | 9.7 |

The translucency values in the present application are determined using light of a wavelength of 520 nm that passes through a disk of material with a thickness of 2.20-2.30 mm. The references "1×" and "5×" in respect of the translucencies refer to the number of firing steps required to apply the materials. TEC is the thermal extension coefficient, which is determined either in the temperature range of 25-400° C. or in the range of 25-500° C. as described in U.S. Pat. No. 5,453,290.

EXAMPLES 1 AND 2

To obtain all opalescent effect, basic veneering materials A, C and S are blended with an opal glass frit (vile infra) in a proportion of 20 to 40 weight percent. The translucency of the basic veneering materials is inversely related to the expansion of the frit, which is caused by the presence of a crystalline leucite phase. Basic material A contains approximately 22 vol.-%% leucite and basic material C about 30 vol.-% leucite, while composition S is leucite-free.

Two different opal glass frits were produced by blending several mixtures of powdered metal oxides, carbonates or nitrates in the appropriate proportion. The blended powders were fused to form a glass melt followed by quenching, drying, ball milling and seeving using means known in the art (Table 2). The powders formed from either one of these two glasses having a particle size of less than 106 μm are pigmented to obtain a toothlike appearance.

TABLE 2

Composition in wt. - % of two opalescent glass frits

| Component | Ex. 1 | Ex. 2 |
|---|---|---|
| $SiO_x$ | 62.0 | 62.6 |
| $Al_2O_3$ | 10.8 | 11.2 |
| $K_2O$ | 9.6 | 7.6 |
| $Na_2O$ | 7.4 | 7.6 |
| CaO | 3.3 | 0.1 |
| MgO | 2.0 | 0.0 |
| $CeO_2$ | 1.8 | 0.0 |
| $Tb_2O_3$ | 1.9 | 2.3 |
| $P_2O_5$ | 2.0 | 0.0 |
| $CaF_2$ | 0.0 | 9.9 |
| Translucency (%) 520 nm 1x | 57.8 | 66.3 |
| Translucency (%) 520 nm 5x | 49.3 | 56.3 |
| Opalescence 1x | 17.5 | 24.7 |
| Opalescence 5x | 20.8 | 24.7 |
| Firing Temperature, °C. | 900 | 835 |
| Glass Transition Temperature, °C. | 590 | 525 |
| TEC μm/m · K (25 to 400° C.) | 8.5 | 9.7 |
| TEC μm/m · K (25 to 500° C.) | 8.8 | 9.3 |

The opalescence is measured as the calculated difference (ΔC) between the a*- and b*-values according to the CIELAB color space, whereby the sample is measured against a white and against a black background using an artificial D65 light source. Particularly, the opalescence is calculated as the square root of $[(a*)^2+(b*)^2]$.

The opalescence found for Example 1 is based on the crystallization of a fine phosphate phase, while in Example 2 calcium fluoride crystals with an average size of 300 nm are generating opalescence.

Both opalescence glass frits had the same or a better opalescence after they were fired 5 times at their firing temperature. However, their translucency suffers from the light absorption caused by the increase in crystalline phase volume.

COMPARATIVE EXAMPLE 3

In the present example, dental restorations prepared according to the traditional method and using the method of the present invention with the materials described in Example 1 and 2 are compared. The results are depicted in Table 3.

TABLE 3

Composition of ceramic C of transparent, incisal, modifier, and opaque ceramic with opal frit Example 1 and Example 2

| | Component | Transparent | Incisal | Modifier | Opaque |
|---|---|---|---|---|---|
| Traditional | Wt.-% $Y_2O_3$ | 0.05 | 0.05 | 0.05 | 0.0 |
| | Translucency (%) 520 nm 1 | 60.0 | 25.0 | 25.0 | 0.0 |
| | Translucency (%) 520 nm 5 | 60.0 | 25.0 | 25.0 | 0.0 |
| | Fluorescence | 8 | 8 | 4 | 0.0 |
| | Opalescence 1x | 0 | 10.0 | 0 | N/A |
| | Opalescence 5x | 0 | 10.0 | 0 | N/A |
| Method of Invention (Ex. 1 opal Frit, 29%) | Wt.-% $Y_2O_3$ | 0.03 | 0.05 | 0.4 | 3.0 |
| | Translucency (%) 520 nm 1 | 60.0 | 40.0 | 25.0 | 0.0 |
| | Translucency (%) 520 nm 5 | 58.0 | 40.0 | 25.0 | 0.0 |
| | Fluorescence | 2 | 4 | 10 | 0.0 |
| | Opalescence 1x | 10.4 | 8.0 | 0 | N/A |
| | Opalescence 5x | 12.7 | 8.0 | 0 | N/A |
| Method of Invention (Ex. 2 opal Frit, 29%) | Wt.-% $Y_2O_3$ | 0.03 | 0.05 | 0.4 | 3.0 |
| | Translucency (%) 520 nm 1 | 62.4 | 40.0 | 25.0 | 0.0 |
| | Translucency (%) 520 nm 5 | 60.7 | 40.0 | 25.0 | 0.0 |
| | Fluorescence | 2 | 4 | 10 | 0.0 |
| | Opalescence 1x | 11.7 | 8.0 | 0 | N/A |
| | Opalescence 5x | 8.1 | 6.0 | 0 | N/A |

The degree of fluorescence is determined using a fluorescence indicator which was specially adjusted for this purpose. The indicator contains 10 discs numbered from 1 to 10 whereby disc 1 has the lowest concentration of fluorescent and disc 10 the highest concentration of fluorescent material.

Opal glass frit Ex. 1 gave an increase in opalescence after 5 firings.

The firing temperature of basic veneering material C is 860° C. and this is 40° C. lower than the firing temperature of Ex. 1. The likelihood that Ex. 1 will react with the basic veneering material C is therefore small.

Opal glass frit Ex. 2 gave a decrease after repeated firings because the firing temperature is 25° C. lower than the basic veneering material C.

For both opal frits the translucency decreases after 5 firings due to a decrease of translucency in the basic veneering material.

COMPARATIVE EXAMPLE 4

In the present example, dental restorations prepared according to the traditional method and using the method of the present invention with the materials described in Examples 1 and 2 are compared. The results are depicted in Table 4.

TABLE 4

Composition of ceramic A of transparent, incisal, modifier, and opaque ceramic with opal frit Ex. 1 and Ex. 2

| | Component | Transparent | Incisal | Modifier | Opaque |
|---|---|---|---|---|---|
| Traditional | Wt.-% $Y_2O_3$ | 0.05 | 0.05 | 0.05 | 0.0 |
| | Translucency (%) 520 nm 1 | 50.0 | 25.0 | 25.0 | 0.0 |
| | Translucency (%) 520 nm 5 | 50.0 | 25.0 | 25.0 | 0.0 |
| | Fluorescence | 8 | 8 | 4 | 0.0 |
| | Opalescence 1x | 0 | 10.0 | 0 | N/A |
| | Opalescence 5x | 0 | 10.0 | 0 | N/A |
| Method of The Invention (Ex. 1 opal Frit, 29%) | Wt.-% $Y_2O_3$ | 0.03 | 0.05 | 0.4 | 3.0 |
| | Translucency (%) 520 nm 1 | 70.2 | 40.0 | 25.0 | 0.0 |
| | Translucency (%) 520 nm 5 | 66.3 | 40.0 | 25.0 | 0.0 |
| | Fluorescence | 2 | 4 | 10 | 0.0 |
| | Opalescence 1x | 10.7 | 8.0 | 0 | N/A |
| | Opalescence 5x | 14.3 | 8.0 | 0 | N/A |
| Method of The Invention (Ex. 2 opal Frit, 29%) | Wt.-% $Y_2O_3$ | 0.03 | 0.05 | 0.4 | 3.0 |
| | Translucency (%) 520 nm 1 | 65.3 | 40.0 | 25.0 | 0.0 |
| | Translucency (%) 520 nm 5 | 67.0 | 40.0 | 25.0 | 0.0 |
| | Fluorescence | 2 | 4 | 10 | 0.0 |
| | Opalescence 1x | 11.0 | 8.0 | 0 | N/A |
| | Opalescence 5x | 7.7 | 6.0 | 0 | N/A |

Opal glass frit Ex. 1 gave an increase in opalescence after 5 firings. The firing temperatures of basic veneering material C is 900° C. and this is the same as the firing temperature of Ex. 1. The likelihood that Ex. 1 will react with the basic veneering material A is therefore small.

Opal glass frit Ex. 2 gave a strong decrease after repeated firings because the firing temperature is 65° C. lower than the basic veneering material A.

COMPARATIVE EXAMPLE 5

In the present example, the dental restorations prepared according to the traditional method and using the method of the present invention with the materials described in Examples 1 and 2 are compared. The results are depicted in Table 5.

TABLE 5

Composition of ceramic S of transparent, incisal, modifier, and opaque ceramic with opal fit Ex. 1 and Ex. 2

| | Component | Transparent | Incisal | Modifier | Opaque |
|---|---|---|---|---|---|
| Traditional | Wt.-% $Y_2O_3$ | 0.05 | 0.05 | 0.05 | 0.0 |
| | Translucency (%) 520 nm 1 | 80.0 | 25.0 | 25.0 | 0.0 |
| | Translucency (%) 520 nm 5 | 80.0 | 25.0 | 25.0 | 0.0 |
| | Fluorescence | 8 | 8 | 4 | 0.0 |
| | Opalescence 1x | 0 | 10 | 0 | N/A |
| | Opalescence 5x | 0 | 10 | 0 | N/A |
| New Method (Ex. 1 opal Frit, 29%) | Wt.-% $Y_2O_3$ | 0.03 | 0.05 | 0.4 | 3.0 |
| | Translucency (%) 520 nm 1 | 72.0 | 40.0 | 25.0 | 0.0 |
| | Translucency (%) 520 nm 5 | 70.0 | 40.0 | 25.0 | 0.0 |
| | Fluorescence | 2 | 4 | 10 | 0.0 |
| | Opalescence 1x | 10.4 | 9.0 | 0 | N/A |
| | Opalescence 5x | 12.7 | 10.0 | 0 | N/A |
| New Method (Ex. 2 opal Frit, 29%) | Wt.-% $Y_2O_3$ | 0.03 | 0.05 | 0.4 | 3.0 |
| | Translucency (%) 520 nm 1 | 68.0 | 40.0 | 25.0 | 0.0 |
| | Translucency (%) 520 nm 5 | 66.0 | 40.0 | 25.0 | 0.0 |
| | Fluorescence | 2 | 4 | 10 | 0.0 |
| | Opalescence 1x | 11.7 | 8.7 | 0 | N/A |
| | Opalescence 5x | 12.8 | 9.7 | 0 | N/A |

Both opal lass frits Ex. 1 and Ex. 2 gave an increase in opalescence after 5 firings. The firing temperature of basic veneering material S is 830° C., which for Ex. 1 is 70° C. and for Ex. 2 30° C. lower than the firing temperature basic veneering material S. The likelihood that Ex. 1 and Ex. 2 will react with the basic veneering material S is therefore small.

What is claimed is:

1. Dental restoration comprising one or more opaque layers covered by one or more other porcelain layers, the opaque layers being situated closer to the core than the one or more other porcelain layers,
   wherein at least one of the one or more opaque layers contains a fluorescent material,
   wherein the one or more other porcelain layers are predominately transparent and opalescent;
   wherein the one or more other porcelain layers comprise at least one incisal layer and at least one dentin layer, and
   wherein a modifier containing fluorescent material is present between (a) the incisal layer and the dentin layer, (b) the dentin layer and an opaque/dentin layer, or a combination of both (a) and (b).

2. The dental restoration of claim 1, wherein the fluorescent material is present in an amount of at least 0.1 wt. % in the modifier layer between the incisal layer and the dentin layer.

3. The dental restoration of claim 2, wherein the fluorescent material of the modifier layer comprises yttrium oxide.

4. Method of layering porcelain on a structure of metal or ceramic comprising the steps of applying a first layer or first layers of an opaque liner material containing a fluorescent material and in a subsequent step applying one or more layers of a translucent, opalescent material, the one or more layers including at least one incisal layer and at least one dentin layer, and
    wherein a modifier containing fluorescent material is applied between (a) the incisal layer and the dentin layer, (b) the dentin layer and an opaque/dentin layer, or a combination of both (a) and (b).

5. The method of claim 4, wherein the fluorescent material is present in an amount of at least 2 wt. % in the opaque liner material, drawn to the total weight of the opaque liner material.

6. The method of claim 5, wherein the fluorescent material comprises yttrium oxide.

7. The method of claim 4, wherein the translucent, opalescent material contains less than 0.05 wt. % fluorescent material.

8. The method of claim 4, wherein at least 10% of an opal glass frit is used as the translucent, opalescent material.

9. The method of claim 4, wherein the translucent, opalescent material has a translucency of more than 30%.

10. The method of claim 4, wherein transparent porcelain layers are applied which consist of 10-100 wt. % opal glass frit with the following composition in wt. %: 45-70% $SiO_2$, 0-20% $Al_2O_3$, 0-20% $K_2O$, 0-15% $Na_2O$, 0-5% CaO, 0-3% MgO, 0-4% $CeO_2$, 0-4% $Tb_2O_3$, 1-10% $P_2O_5$, 0-1% $CaF_2$, 0-2% $Li_2O$, and 0-5% $Sb_2O_3$.

11. The method of claim 4, wherein transparent porcelain layers are applied which consist of 10-100 wt. % opal glass frit with the following composition in wt. %: 45-70%, $SiO_2$, 0-20% $Al_2O_3$, 0-20% $K_2O$, 0-15% $Na_2O$, 0-5% CaO, 0-3% MgO, 0-4% $CeO_2$, 0-4% $Tb_2O_3$, 0-2% $P_2O_5$, 5-15% $CaF_2$, 0-2% $Li_2O$ and 0-5% $Sb_2O_3$.

12. The method of claim 4, wherein the fluorescent material is present in an amount of at least 0.1 wt. % in the modifier layer between the incisal layer and the dentin layer.

13. The method of claim 12, wherein the fluorescent material of the modifier layer comprises yttrium oxide.

14. The method of claim 8, wherein the opal glass frit of the translucent, opalescent material comprises a firing temperature that is not lower than 25° C. than the firing temperature of the material on which it is applied to secure the two materials while not generally reacting with one another.

15. The method of claim 4, wherein
    (i) fluorescent material is present in an amount of less than 0.05 wt. % in the translucent, opalescent material;
    (ii) the fluorescent material is present in an amount of at least 2 wt. % in the opaque liner material;
    (iii) the fluorescent material is present in an amount of at least 0.1 wt. % in the modifier layer between the incisal layer and the dentin layer
    (iv) at least 10% of an opal glass frit is used as the translucent, opalescent material; and
    (v) the translucent, opalescent material has a translucency of more than 30%.

16. The method of claim 15, wherein the opal glass frit of the translucent, opalescent material comprises a firing temperature that is not lower than 25° C. than the firing temperature of the material on which it is applied to secure the two materials while not generally reacting with one another.

17. The method of claim 16, wherein the fluorescent material in the opaque liner material, the translucent, opalescent material, and the modifier layer between the incisal layer and the dentin layer comprises yttrium oxide.

* * * * *